(12) United States Patent
Ithapu et al.

(10) Patent No.: US 9,687,199 B2
(45) Date of Patent: Jun. 27, 2017

(54) MEDICAL IMAGING SYSTEM PROVIDING DISEASE PROGNOSIS

(71) Applicant: Wisconsin Alumni Research Foundation, Madison, WI (US)

(72) Inventors: Vamsi K Ithapu, Madison, WI (US); Vikas Singh, Madison, WI (US); Sterling C Johnson, Fitchburg, WI (US); Ozioma C Okonkwo, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/848,903

(22) Filed: Sep. 9, 2015

(65) Prior Publication Data

US 2016/0073969 A1 Mar. 17, 2016

Related U.S. Application Data

(60) Provisional application No. 62/050,592, filed on Sep. 15, 2014.

(51) Int. Cl.
| | |
|---|---|
| *G06K 9/00* | (2006.01) |
| *A61B 5/00* | (2006.01) |
| *G06K 9/62* | (2006.01) |
| *A61B 5/055* | (2006.01) |
| *A61B 6/03* | (2006.01) |
| *A61B 6/00* | (2006.01) |

(52) U.S. Cl.
CPC .......... *A61B 5/7267* (2013.01); *A61B 5/0042* (2013.01); *A61B 5/055* (2013.01); *A61B 5/7203* (2013.01); *A61B 5/7271* (2013.01); *A61B 5/742* (2013.01); *A61B 6/037* (2013.01); *A61B 6/4417* (2013.01); *A61B 6/5247* (2013.01); *G06K 9/6217* (2013.01); *G06K 9/6293* (2013.01); *A61B 6/501* (2013.01); *A61B 2560/0475* (2013.01)

(58) Field of Classification Search
None
See application file for complete search history.

(56) References Cited

U.S. PATENT DOCUMENTS

| | | | | |
|---|---|---|---|---|
| 7,383,237 B2 * | 6/2008 | Zhang | ................... | G06K 9/623 706/20 |
| 2009/0245603 A1 * | 10/2009 | Koruga | .................. | A45D 44/00 382/128 |

(Continued)

OTHER PUBLICATIONS

Hinrichs, Chris et al.; "MKL-based sample enrichment and customized outcomes enable smaller AD clinical trials." InMachine Learning and Interpetation in Neuroimaging: pages.cs.wisc.edu; pp. 1-8; 2012 US.

(Continued)

*Primary Examiner* — Shervin Nakhjavan
(74) *Attorney, Agent, or Firm* — Boyle Fredrickson, S.C.

(57) ABSTRACT

A medical imaging system that processes input data (imaging and/or non imaging) having high dimensionality and few samples to learn from, by using multiple ranks of machine learning modules each dealing with a separate portion of the clinical data. The outputs of the individual machine learning modules are the combined to provide a result reflective of the complete image data set.

20 Claims, 3 Drawing Sheets

(56) References Cited

U.S. PATENT DOCUMENTS

| | | | |
|---|---|---|---|
| 2012/0008838 A1* | 1/2012 | Guyon | G06F 19/345 382/128 |
| 2014/0037172 A1* | 2/2014 | Madabhushi | G06K 9/6232 382/131 |
| 2016/0081663 A1* | 3/2016 | Chen | A61B 5/065 600/425 |

OTHER PUBLICATIONS

Heung-Il Suk et al.; "Hierarchical feature representation and multimodal fusion with deep learning for AD/MCI diagnosis" Author Manuscript Published in final edited form as: NeuroImage 101: Nov. 1, 2014; pp. 1-38; US.

* cited by examiner

MEDICAL IMAGING SYSTEM PROVIDING DISEASE PROGNOSIS

CROSS REFERENCE TO RELATED APPLICATION

This application claims the benefit of U.S. provisional 62/050,592 filed Sep. 15, 2015 and hereby incorporated by reference.

STATEMENT REGARDING FEDERALLY SPONSORED RESEARCH OR DEVELOPMENT

This invention was made with government support under AG040396 awarded by the National Institutes of Health and 1252725 awarded by the National Science Foundation. The government has certain rights in the invention.

BACKGROUND OF THE INVENTION

The present invention provides a medical imaging system that can process medical imaging data to present a disease prognosis based on limited clinical data.

Modern medical diagnostic tools such as magnetic resonance imaging (MRI) and positron emission tomography (PET) provide clinicians with a wealth of data that promises to greatly advance our ability to measure and predict disease progression. In one example, there is strong evidence that Alzheimer's disease manifest in such brain imaging data years before the onset of clinical or cognitive symptoms.

The amount of data output by diagnostic imaging tools such as MRI practically exceeds the analysis abilities of individual diagnosticians and accordingly specialized machine learning systems have been used with imaging systems to process this information. As is understood in the art, such machine learning systems provide circuitry that can "learn" to analyze data by a training process that uses a set of known examples that form a training set. For example, a training set for the detection of Alzheimer's disease may provide imaging information from a set of subjects with two sub-groups. The first sub-group corresponds to those subjects that are cognitively healthy whereas the other subgroup includes subjects who have been diagnosed with Alzheimer's disease. First, the training set is presented to the machine learning system which learns to make the correct prognosis of Alzheimer's disease or no Alzheimer's disease from the imaging data of the training set. Next, imaging data of a new patient, whose prognosis is unknown, is applied to the trained machine learning system to obtain a prognosis for that new patient.

A serious obstacle to the training of machine learning systems using clinical data is the mismatch between the number of dimensions of the clinical data (the total number of measurements obtained from all types of data collecting instruments, for example MRI and PET etc.) and the number of samples (for example, patients) in the clinical trial. Often, the number of patients in a clinical trial (and hence the number of samples in a potential training set) is relatively limited (for example, less than 1000) while the dimensions of data obtained from the imaging equipment can be in the many millions. In these cases, where the dimensionality of the data far exceeds the number of samples, the machine learning system will almost surely not be able to learn the underlying concept (the distinction between disease and no disease) due to the few number of samples to learn from.

This problem of unnecessary over fitting is fundamentally inevitable given the cost and difficulty of performing clinical studies with larger numbers of patients and the increasingly powerful medical imaging devices that provide increasing dimensions of measurement.

SUMMARY OF THE INVENTION

The present inventors have developed a medical imaging system that provides a machine learning architecture that can learn from clinical data with high dimensionality but a low number of samples incident to a small clinical study. Generally, the system divides up the data (splits the high dimensional data into multiple sets of smaller dimensions) for independent training of different "smaller" machine learning modules so that significant input data will be exposed and emphasized during the training, without forcing the system to be lost in the high dimensionality of the data. Once exposed and emphasized, the outputs of multiple such smaller machine learning modules are combined, for example, by a second machine learning module, to provide an overall result.

Specifically then, the present invention provides a medical image processor system including at least one medical imaging device providing image data with multiple dimensions identifying physiological characteristics of a patient and is stored in an electronic memory. A plurality of first rank machine learning modules are provided receiving input data and producing output data based on predetermined (i.e., trained or learned from training data) weights. Allocator circuitry divides the received image data from the electronic memory into a plurality of blocks associated with different subsets of the dimensions of the image data, and provides different blocks to different of the first rank machine learning modules as input data. A combiner receives output data from these first rank machine learning modules and combines it to provide an output providing a diagnosis based on the image data. The predetermined weights of the first rank machine learning modules are produced by separately training the plurality of first rank machine learning modules with a training set limited to the same subsets of the dimensions of the image data processed by the first rank machine learning modules.

It is thus a feature of at least one embodiment of the invention to provide a medical imaging system that can provide useful disease prognosis information. In this regard, it is a further feature of at least one embodiment of the invention to permit the processing of data having a high dimension, such as image data from single or multiple data collecting instruments like MRI, PET etc., to extract useful clinical prognoses based on a limited sampling of cases where a prognosis is known. By dividing the dimensionality of the data among multiple first rank learning modules, the risk of overfitting of the data is substantially reduced while ensuring sufficient generalizability by learning the actual complex concept of disease or no disease.

Groups of multiple first rank machine learning modules may receive image data from each block and the first rank machine learning modules within each group may operate according to different parameters (also referred to as hyperparameters since they are "fixed" ahead of time and are not learned or varied during the training process) defining their learning capability.

It is thus a feature of at least one embodiment of the invention to vary the learning capabilities of multiple machine learning modules to better expose important dimensions of the data among the extremely large number of data dimensions. These different parameters may include learning rate, for example, by controlling a steepness of a compression curve used in the activation function of the machine learning modules, and/or a number of hidden layers in a machine learning module providing a multilayer network.

It is thus a feature of at least one embodiment of the invention to provide a solution adaptable to common network-type machine learning modules.

The combiner may also be a machine learning module for receiving input data and providing output data based on predetermined weights and may receive outputs from the first rank machine learning modules and have predetermined weights obtained by training the second rank machine learning modules with outputs of the first rank machine learning modules, the former using the training set limited to the same subsets of the dimensions of the image data processed by the first rank machine learning modules to produce training outputs for at least one second rank machine learning module.

It is thus a feature of at least one embodiment of the invention to make use of the capabilities of the learning system to combine the multiple outputs of the first rank of machine learning modules into a single overarching prognostic value.

The first rank machine learning modules and the combiner may both be implemented in the form of denoising autoencoders.

It is thus a feature of at least one embodiment of the invention to make use of well-characterized machine learning module designs.

At least one medical imaging device may be selected from the group consisting of magnetic resonance imaging and positron emission tomography machines.

It is thus a feature of at least one embodiment of the invention to work with common medical imaging systems producing data with high dimensionality.

The training set may provide multiple samples associated with different patients each sample having multiple dimensions of data, with the number of dimensions of data exceeding 100000 and the number of samples being less than 1000.

It is thus a feature of at least one embodiment of the invention to accommodate the mis-match between sample size and data dimensions often associated with clinical trials.

The data may include voxel data providing physical measurements of patient tissue over a regular range of volumetric coordinates.

It is thus a feature of at least one embodiment of the invention to accommodate the processing of medical images that inherently provides high data dimensionality in the number of voxels.

The electronic memory may further include a training set of training image data linked to known prognoses and further including a training circuit for providing the training weights using the training set of image data.

It is thus a feature of at least one embodiment of the invention to provide a medical imaging system that can train itself for different disease prognostics.

The system may further include a noise injector injecting noise into the data of the subsets during training.

It is thus a feature of at least one embodiment of the invention to reduce overfitting by perturbing the training set data with noise.

The electronic memory may further include non-image clinical data and the allocator circuitry may divide the non-image clinical data into the plurality of blocks.

It is thus a feature of at least one embodiment of the invention to permit the system to use non-image dimensions for prognostics.

The training set may be images of brains of patients at a first time together with diagnoses of the patients with respect to Alzheimer's disease at a second time.

It is thus a feature of at least one embodiment of the invention to provide an imaging system that can better predict the onset of Alzheimer's disease.

The invention may be used to select individuals for a clinical trial of a treatment for a disease based on the prognostic output.

It is thus a feature of at least one embodiment of the invention to provide a system for enriching clinical trials to improve the quality of the data from those trials.

These particular objects and advantages may apply to only some embodiments falling Within the claims and thus do not define the scope of the invention.

DETAILED DESCRIPTION OF THE PREFERRED EMBODIMENT

Hardware Elements

Figure 1:
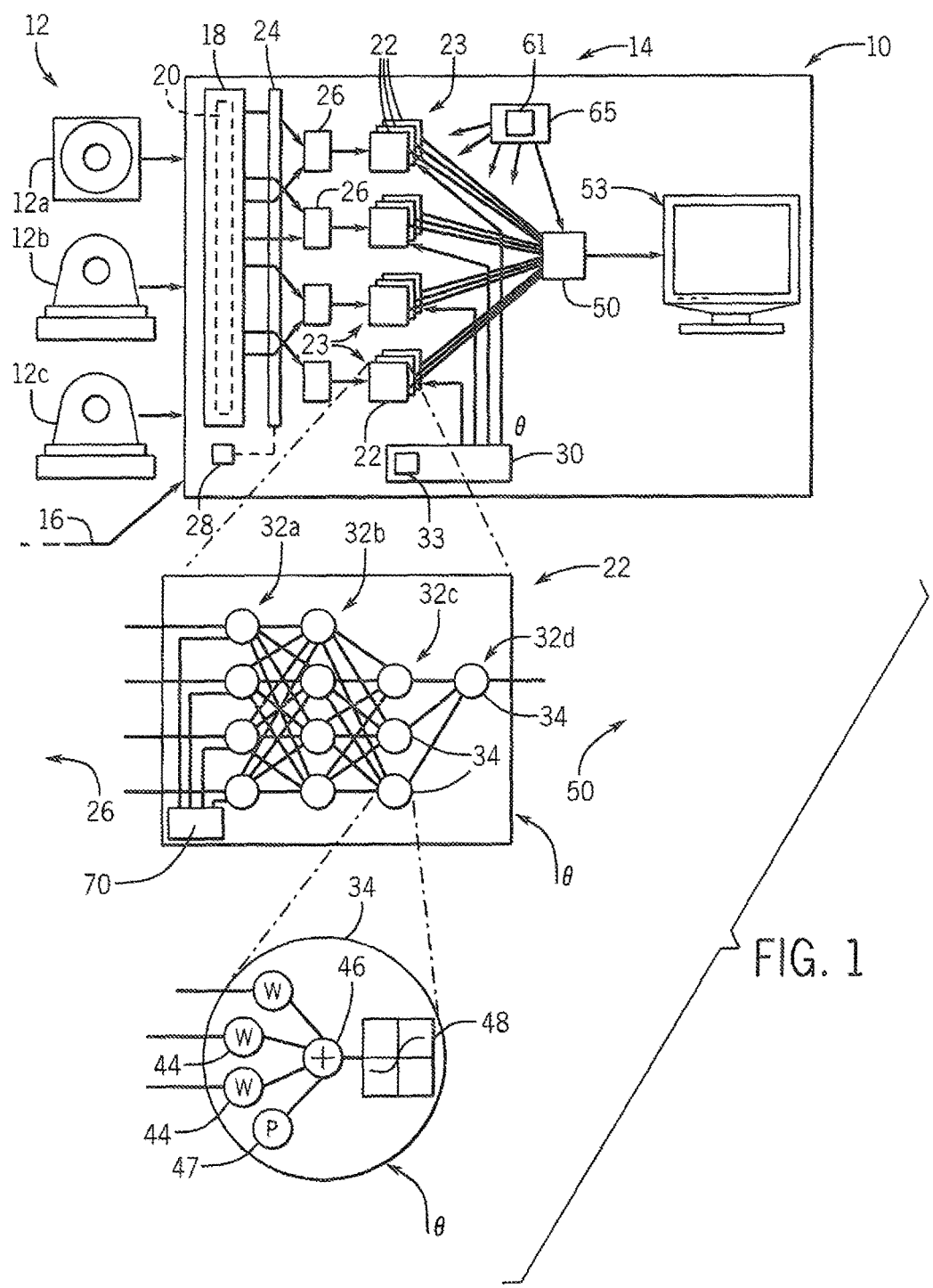
FIG. 1 is a block diagram of the medical imaging system per the present invention providing multiple machine learning modules and showing an expanded view of one typical module and a node making up a network of the module.

Referring now to FIG. 1, a medical imaging system 10 may employ one or more medical imaging sources 12 providing data to a processing engine 14. In the example of a medical imaging system 10 for diagnosing Alzheimer's disease, three medical imaging sources 12 may be employed including: an magnetic resonance imaging (MRI) machine 12a, a positron emission tomography (PET) machine 12b for providing amyloid data and a PET machine 12c for providing Fludeoxyglucose (FDG) data. The medical imaging system 10 may also accept non-image data sources 16 such as degree of cognitive impairment and parental family history.

A set of data 20 collected from these medical imaging sources 12 and non-image data sources 16 may be provided to the processing engine 14 to be stored in electronic memory 18. Generally this set of data 20 has dimensions v much greater than the number of samples n.

The set of data 20 is mapped to a set of stacked de-noising autoencoders 22 according to a mapper 24. Generally the mapper 24 will divide the set of data 20 up into a set of B subset blocks 26 corresponding in number to the number of stacked de-noising autoencoders 22. The subset blocks 26 need not be mutually exclusive that is a voxel may belong to multiple subset blocks 26); however, in one embodiment, disjoint data is selected from the set of data 20 using a uniform random distribution according to a mapping stored in a mapping memory 28. This mapping $\tau(v)$ is determined during training and is preserved during operation as will be described below.

The stacked de-noising autoencoders 22 will be divided into groups 23 of T and each of the different stacked de-noising autoencoders 22 in one group 23 will receive the same data of a single one of the subset. On the other hand, the different stacked de-noising autoencoders 22 in each group will receive a different randomized set of parameters θ from parameter variation circuit 30 according to a parameter variation memory 33. The parameters θ control the internal operation of the de-noising autoencoders as will be discussed below and are preserved according to a selection made during training as will also be discussed below.

Each stacked de-noising autoencoder 22 may include a network of multiple layers 32 of nodes 34, here shown as an input layer 32a, two successive hidden layers 32b and 32c, and an output layer 32d. Each node 34 of the input layer 32a receives one data element from each block 26 of $s_b$ data elements and passes it to multiple nodes 34 of the succeeding hidden layer 32b which in turn processes that data and provides it to multiple nodes 34 of the second hidden layer 34c that similarly produces outputs collected by the nodes 34 of the output layer 32d which are then consolidated by a single output classifier node 34 of output layer 32d as is generally understood in the art.

The nodes 34 of all but the input layer 32a will provide for weighting multipliers 44 receiving the inputs from the outputs of the previous nodes 34 and applying a weight to those inputs by multiplying them by a weight W. The weighted inputs and an offset value 47 (p) are then summed by adder 46 and then provided to an activation processor 48 which applies an activation function, typically a sigmoid function, having a range from 0 to 1. The activation processor 48 thus compresses the sum of the inputs to the node 34 to an output in a range from 0 to 1.

In this regard, each node 34 generally implements a function:

$$h = \sigma\left(\sum_i (W_i x_i + p)\right)$$

where h is the output of the node 34, $W_i$ is the weight associated with each input $x_i$, p is an offset value, and σ( ) is the sigmoid function. The values of the weights W and offsets p are determined during the training steps as will be discussed.

Each of the outputs of the de-noising autoencoders 22 of the output layer 32d are then received by a consolidating stacked de-noising autoencoder 50 having a construction generally identical to that of the stacked de-noising autoencoders 22. The de-noising autoencoder 50 serves to combine outputs from the de-noising autoencoders 22 and provides a single diagnostic output value, for example, indicating in a range from 0 to 1 likelihood of a given disease such as Alzheimer's disease. In this case, the value of zero may represent the highest likelihood of Alzheimer's disease and the value one indicating the lowest likelihood of Alzheimer's disease. The invention contemplates that the consolidating stacked de-noising autoencoder 50 may be replaced with other mechanisms including, for example, a circuit providing a simple regression (for example, a ridged regression). Generally any circuit that provides a regression can be used. This output from the dc-noising autoencoder 50 may be provided to a user interface 53 such as a display screen in the form of a numeric readout, gauge, or the like to provide information to a medical professional about the analysis of the medical image data.

Diagnostic Procedure

Figure 2:
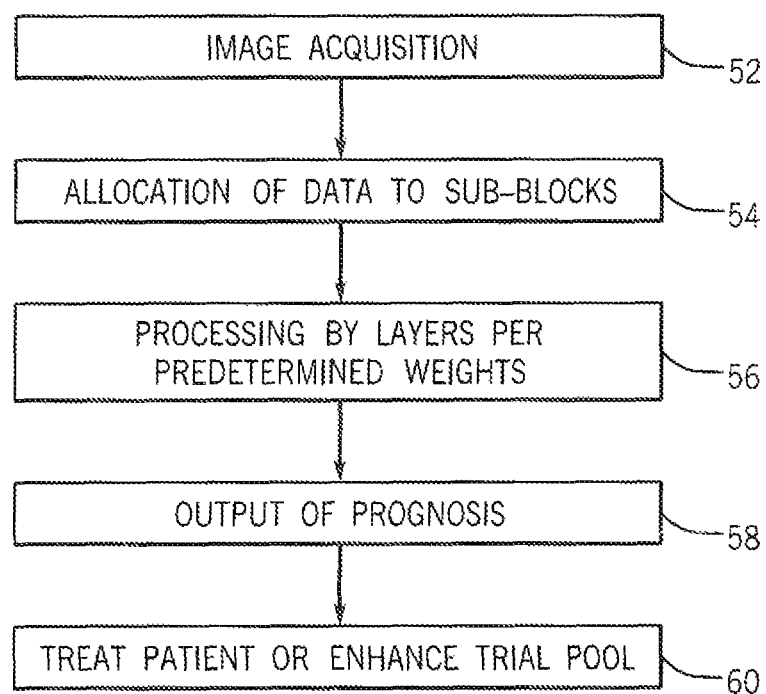
FIG. 2 is a flowchart of the steps of using the system of claim 1 in making a prognosis after training.

Referring then to FIGS. 1 and 2, during operation, the medical imaging system 10 acquires medical imaging data as indicated by process block 52 through the imaging sources 12. This data is then allocated by mapper 24, per process block 54, into different blocks 26 which are operated on by the separate de-noising autoencoders 22.

The output of these the de-noising autoencoders 22 is then consolidated, as indicated by process block 56, by the consolidating de-noising autoencoder 50 which provides an output as indicated by process block 58 to a clinician or the like. This output data may be used to provide guidance to the physician or healthcare professional with respect to a particular patient or may be used to select patients for participation in a clinical trial as indicated by process block 60. For example, information predicting the development of Alzheimer's disease may be used in a clinical trial developing possible treatments of Alzheimer's disease. By selecting patients that are predisposed toward Alzheimer's disease, the trial is enriched in the effort of long-term treatment, tracking and analysis is not expended on individuals that are likely not to develop the disease for other reasons. Using this enhancement technique the sample size of n individuals in the study may be leveraged.

Training Procedure

Figure 3:
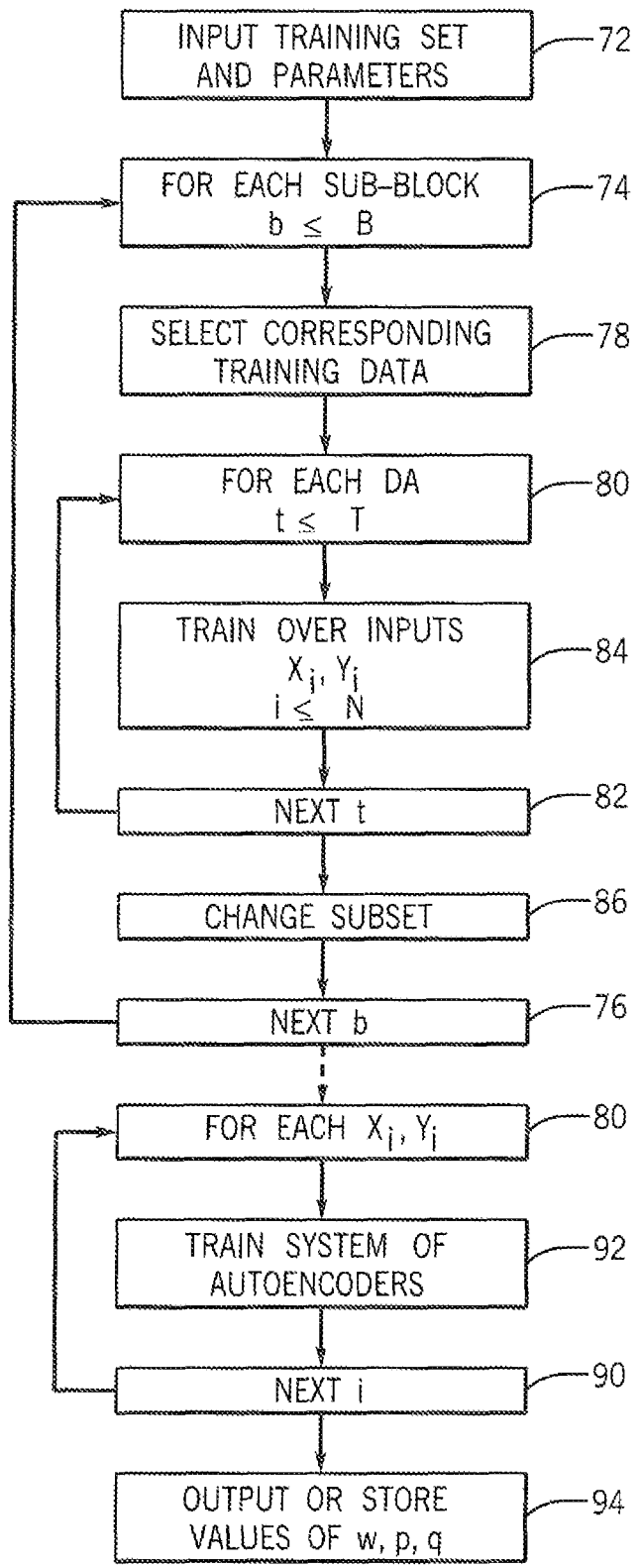
FIG. 3 is a flowchart of the training process of the medical imaging system of FIG. 1.

Referring now to FIGS. 1 and 3, before the step of process block 52 described above with respect to FIG. 2, the weights W, the mapping of the set of data 20 to the blocks 26, and the particular parameters θ provided to each of the de-noising autoencoders 22 must go through a training process performed by training circuit 65. The training process uses a training set 61 designated $\{x_i, y_i\}$ linking values of $x_i$ for a set of patients corresponding generally to the dimensions of the set of data 20 and, at a first time, to the values $y_i$ indicating whether they develop Alzheimer's disease at a later time. Generally, in this embodiment, training each de-noising autoencoder 22 (and the de-noising autoencoder 50) attempts to minimize a loss function L between input values $x_i$ of the training set and a reconstruction of those inputs according to the equation:

$$\hat{x}_i = \sigma\left(\sum_i (W^T h_i + q)\right)$$

where $W^T$ is the transposition of the vector $W_i$; as follows:

$$\mathcal{Z}_{da}(\{x_i\}_1^n, \theta) := \arg\min_{W,p,q} \sum_{i=1}^n \mathbb{E}_{\tilde{x} \sim \gamma(\tilde{x}|x)} \mathcal{L}(x_i, \sigma(W^T \sigma(W x_i + p) + q))$$

In this equation, γ is point wise stochastic corruption (noise) introduced into the input of each node as shown in FIG. 1 by noise injector 70. In general, $y_i$ will be the output hi for the final layer.

$$\mathcal{Z}_{sda}(\{x_i\}_1^n, L, \theta) := \sum_{l=0}^{L-1} \mathcal{Z}_{da}(\{h_i^l\}_1^n, \theta) : h_i^l = \sigma(W^l h_i^{l-1} + p^l) : h_i^0 = x_i$$

Here θ represents the parameters adjusted by the parameter variation circuit 30 which are randomized among each of the de-noising autoencoders 22 within a group 23 of T, as described above, and stored in parameter variation memory 33 to be used later during the diagnostic procedure. The parameters θ include the corruption rate of the noise level λ, the learning rate, the number of layers and the hidden layer length, all of which are varied among the de-noising autoencoders 22 of each group 23. In one example, only the noise level and learning rate are varied, the number of layers is fixed to three and all hidden layers across "all" the blocks (i.e. all the stacked denoising autoencoders) are the same (approximately D/B where D is the total number of dimensions of the data, and B is the total number of blocks). This example should not be considered limiting.

The de-noising autoencoders 22 greedily concatenate each layer. That is, layer l provides the uncorrupted inputs for the (l+1) layer to the right.

The Transformations:

$$\{W^l, p^l, q^l\}_l^L$$

provide a "warm-start" for supervised training where one compares the output of the l-th layer to $\{y_i\}_1^n$ where $y_i$ is the output data of the training set.

A summary of this training process is provided below in the form of pseudocode:

---
Algorithm rDA Blocks training
---

Input: $\theta_t \sim \Theta$, V, B, $s_B$, L, T, D ~
$\{x_i, y_i\}_1^n$, λ
Output: $(W_{b,t}^l, p_{b,t}^l, q_{b,t}^l)$
  for b = 1, ..., B do
    $I_b \sim \tau(V)$
    for t = 1, ..., T do
      $(W_{b,t}^l, p_{b,t}^l, q_{b,t}^l) \leftarrow Z_{sda}(D, L, I_b, \theta_t)$
    end for
    $\tau(V) \leftarrow \text{Reweigh}(\tau(V), I_b)$
  end for|

---

Referring now to FIGS. 1 and 3, this training process begins as shown by process block 72 by inputting a training set and the necessary parameters for the number of blocks 26 as well as the general parameters of the de-noising autoencoders 22. In one embodiment, the training set for the example of Alzheimer's disease may come from ADNI2 (Alzheimer's Disease Neuroimaging Initiative).

The mapping τ(v) for each block 26 employed by the mapper 24 is then determined, for example, by using a random selection from a set of data 20 employing a uniform distribution to create blocks of length $s_b$. This partitioning of the data is stored in mapping memory 28 to be used during the diagnostic procedure. As indicated by process blocks 74 and 76, the data of the blocks 26 will then be processed.

For each block 26, a corresponding portion of the training set is selected according to the given mapping τ(v) stored in the mapping memory 28 per process block 78. Then, for each de-noising autoencoder 22 in a given group 23 associated with a given block 26, as indicated by process blocks 80 and 82, the subset of the training set is applied to the de-noising autoencoders 22 for training over the different samples n of the training set per process block 84. Note that only the training set dimensions corresponding to the block 26 are used for each set of de-noising autoencoders 22 associated with the block 26, but all samples of the training set are employed.

In this training, the de-noising autoencoders 22 attempt to reproduce the training set outputs $y_i$ with their outputs $h_i$.

As noted above, the different de-noising autoencoders 22 of each given group 23 have each received different parameters θ from the parameter variation circuit 30 and these parameters are stored in parameter variation memory 33 so that identical parameters may be used during normal diagnostic processing. At the conclusion of the loop formed by process blocks 80 and 82, a new subset of the training set is obtained for the next block 26 and next group 23 of de-noising autoencoders 22 as indicated by process block 86.

Once each of the T de-noising autoencoders 22 of each group 23 have been trained with the appropriate subset of the dimensions of the training set, then at process block 88 and 90, a loop is formed so that the training set data for all blocks 26 are applied to all de-noising autoencoders 22 one sample at a time and the outputs of the de-noising autoencoders 22 provided to the integrating de-noising autoencoder 50 that composes all the outputs from the denoising autoencoders to produce one single output which is then compared to $y_i$. The output of de-noising autoencoder 50 is then trained per process block 92 to match the appropriate $y_i$ value of the training set at the output of the consolidating de-noising autoencoder 50.

At the conclusion of this process, indicated by process block 94, the learned values of W, p, and q are stored for use in the diagnostic procedure of FIG. 2.

Additional details of this process are described in Ithapu, V. K., Singh, V., Okonkwo, O. C., Chappell, R. J., Dowling, N. M., Johnson, S. C., & Alzheimer's Disease Neuroimaging Initiative. (2015), Imaging-based enrichment criteria using deep-learning algorithms for efficient clinical trials in mild cognitive impairment, Alzheimer's & Dementia, doi: 10.1016/j.jalz.2015.01.010; and Ithapu, V. K., Singh, V., Okonkwo, O., & Johnson, S. C. (2014), Randomized Denoising Autoencoders for Smaller and Efficient Imaging Based AD Clinical Trials, in Medical Image Computing and Computer-Assisted intervention—MICCAI 2014 (pp. 470-478), Springer International Publishing, both hereby incorporated by reference to the extent that they are fully supported by disclosure of the appendices of the provisional application 62/050,592 cited above.

Generally the present invention may be implemented through a variety of different hardware approaches including, for example, dedicated circuitry including neural network processors such as the CM1K neural network chip providing 1,024 neurons working in parallel and commercially available from Recognetics, Suzhou, New District, China. The same functions may be implemented on a high-speed electronic computer emulating this circuitry References to circuitry or circuits should be understood to include discrete electrical components as well as integrated circuits, field programmable gate arrays and the like and electronic computers executing a program stored in non-transient media either as firmware or software. References to memory, unless otherwise specified, can include one or more computer and accessible memory elements and/or components that can be internal to the computer or external to the computer as accessed via a wired or wireless media including a network.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

The cited references in this document and the other documents comprising this provisional filing are all incorporated by reference.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A medical imaging system comprising:
   at least one medical imaging device providing image data having multiple dimensions identifying physiological characteristics of a patient;
   an electronic memory receiving the image data;
   a plurality of first rank machine learning modules for receiving input data and providing output data based on predetermined weights;
   allocator circuitry dividing the received image data into a plurality of blocks associated with different subsets of the dimensions of the image data, the blocks provided to each of the first rank machine learning modules as input data; and
   a combiner receiving output data from the first rank machine learning modules and combining it to provide an output providing a diagnosis based on the image data;
   a display receiving the output to present a diagnosis;
   wherein the predetermined weights of the first rank machine learning modules are produced by separately training the plurality of first rank machine learning modules with a training set limited to the same subsets of the dimensions of the image data processed by the first rank machine learning modules.

2. The medical imaging system of claim 1 wherein groups of multiple first rank machine learning modules receive image data from each block and wherein the first rank machine learning modules within each group operate according to different parameters defining their learning capability.

3. The medical imaging system of claim 2 wherein the different parameters include learning rate.

4. The medical imaging system of claim 3 wherein the first rank machine learning modules provide an activation function compressing a range of the output of the first rank machine learning modules and the parameter includes a steepness of a compression curve used in the activation function.

5. The medical imaging system of claim 3 wherein the first rank machine learning modules provide a multilayer network of weighting and summing nodes including a first layer, a last layer, and at least one intervening hidden layer and wherein the parameters include a number of nodes in the hidden layer.

6. The medical imaging system of claim 1 wherein the combiner is at least one second rank machine learning module for receiving input data and providing output data based on predetermined weights, wherein at least one second rank machine learning module receives outputs from the first rank machine learning modules; and
   wherein the predetermined weights of at least one second rank machine learning module are obtained by training the second rank machine learning modules with outputs of the first rank machine learning modules using the training set limited to the same subsets of the dimensions of the image data processed by the first rank machine learning modules to produce training outputs for at least one second rank machine learning module.

7. The medical imaging system of claim 6 wherein the plurality of first rank machine learning modules and at least one second rank machine learning module are de-noising autoencoders.

8. The medical imaging system of claim 1 wherein at least one medical imaging device is selected from the group consisting of magnetic resonance imaging and positron emission tomography machines.

9. The medical imaging system of claim 1 wherein the training set provides multiple samples associated with different patients each sample having multiple dimensions of data more than ten thousand and the number of samples being less than one thousand.

10. The medical imaging system of claim 9 wherein the data includes voxel data providing physical measurements of patient tissue over a regular range of volumetric coordinates.

11. The medical imaging system of claim 1 wherein the electronic memory further includes a training set of training image data linked to known prognoses and further including a training circuit for providing the training weights using the training set of image data.

12. The medical imaging system of claim 11 wherein the training circuit independently trains the plurality of first rank machine learning modules using training subsets of the training image data corresponding to the subsets and subsequently trains at least one second rank machine learning module using the training subsets of the training, image data corresponding to the subsets first passing through the first rank machine learning modules to provide training inputs to at least one second rank training module.

13. The medical imaging system of claim 1 further including a noise injector injecting noise into the data of the subsets during training.

14. The medical imaging system of claim 1 wherein the electronic memory further includes non-image clinical data and wherein, the allocator circuitry divides the non-image clinical data into the plurality of blocks.

15. The medical imaging system of claim 1 further including a human machine interface for providing a human-readable prognosis indication providing disease prognosis from medical imaging data.

16. The medical imaging system of claim 1 wherein the at least one medical imaging device is selected from the group consisting of: magnetic resonance imaging (MRI) devices and positron emission tomography (PET) devices and wherein the plurality of first rank machine learning modules, allocator circuitry, and combiner are selected from the group consisting of: dedicated circuitry, neural network processor chips, high speed electronic computers.

17. A method of processing medical image using a medical imaging system having:
- at least one medical imaging device providing image data having multiple dimensions identifying physiological characteristics of a patient;
- an electronic memory receiving the image data;
- a plurality of first rank machine learning modules for receiving input data and providing output data based on predetermined weights;
- allocator circuitry dividing the received image data into a plurality of blocks associated with different subsets of the dimensions of the image data, the blocks provided to each of the first rank machine learning modules as input data; and
- a combiner receiving output data from the first rank machine learning modules and combining it to provide an output providing a diagnosis based on the image data;
- wherein the predetermined weights of the first rank machine learning modules produced by separately training with a training set are limited to the same subsets of the dimensions of the image data processed by the first rank machine learning modules; the method comprising the steps of:
  - (a) independently training the first rank machine learning modules with a training set limited to the same subsets of the dimensions of the image data processed by the first rank machine learning modules to determine the predetermined weights;
  - (b) dividing received image data into a plurality of blocks associated with different subsets of the dimensions of the image data, the blocks provided to each of the first rank machine learning, modules as input data using the allocator circuit;
  - (e) processing the plurality of blocks different from the first rank of machine learning modules according to the predetermined weights; and
  - (d) combining the output of the first rank of machine learning modules to provide a prognostic output of the image data.

18. The method of claim 17 wherein groups of multiple first rank machine learning modules receive image data from each block and wherein the first rank machine learning modules within each group operate according to different parameters defining their learning capability.

19. The method of claim 17 wherein the training set is images of brains of patients with and without diagnoses of Alzheimer's disease.

20. The method of claim 17 further including the step of selecting individuals for a clinical trial of a treatment for a disease based on the prognostic output.

* * * * *